United States Patent
Manso

(10) Patent No.: US 6,390,103 B1
(45) Date of Patent: May 21, 2002

(54) TOOTHPASTE DISPENSING TOOTHBRUSH HAVING FLOSS DISPENSER

(76) Inventor: Shannen Manso, P.O. Box 1407, Flowery Branch, GA (US) 30542-0024

( * ) Notice: Subject to any disclaimer, the term of this patent is extended or adjusted under 35 U.S.C. 154(b) by 0 days.

(21) Appl. No.: 09/641,854

(22) Filed: Aug. 18, 2000

(51) Int. Cl.[7] .............................................. A45D 44/18
(52) U.S. Cl. ...................................... 132/309; 401/270
(58) Field of Search ................................ 132/308, 309, 132/311, 321, 324, 325; 401/195, 52, 183, 268, 270, 275, 276

(56) References Cited

U.S. PATENT DOCUMENTS

| | | | | |
|---|---|---|---|---|
| 1,279,507 A | * | 9/1918 | Briggs | 132/321 |
| 1,711,183 A | * | 4/1929 | Smith | 401/175 |
| 2,900,650 A | * | 8/1959 | Rivero | 401/183 |
| 4,522,524 A | * | 6/1985 | Green | 401/183 |
| 4,615,635 A | * | 10/1986 | Kim | 401/270 |
| 4,622,984 A | * | 11/1986 | Gaebel | 132/84 |
| 4,673,106 A | * | 6/1987 | Fishman | 222/80 |
| 4,934,389 A | * | 6/1990 | Pettiford | 132/325 |
| 5,123,765 A | * | 6/1992 | O'Connell | 401/126 |
| 5,832,940 A | * | 11/1998 | Embry et al. | 132/309 |
| 5,950,641 A | * | 9/1999 | Taveras | 132/309 |

\* cited by examiner

*Primary Examiner*—Nicholas D. Lucchesi
*Assistant Examiner*—David Comstock

(57) ABSTRACT

A dental hygiene assembly for combining a tooth brush, a toothpaste container and a dental floss dispenser. The dental hygiene assembly includes a main member, a head portion, a refill port and a base portion. The main member has a main chamber for containing a quantity of toothpaste. The head portion has a head chamber that is in fluid communication with the main chamber. The head portion has a plurality of bristles for brushing the teeth of a user. A plurality of bristle apertures are positioned between the plurality of bristles. The bristle apertures are selectively in fluid communication with the head chamber. The refill port is designed to couple to a standard toothpaste container to refill the main chamber. In addition, the base member contains a quantity of dental floss.

9 Claims, 4 Drawing Sheets

TOOTHPASTE DISPENSING TOOTHBRUSH HAVING FLOSS DISPENSER

BACKGROUND OF THE INVENTION

1. Field of the Invention

The present invention relates to combination toothbrush and toothpaste containers and more particularly pertains to a new dental hygiene assembly for combining a toothbrush, a toothpaste container and a dental floss dispenser.

2. Description of the Prior Art

The use of combination toothbrush and toothpaste containers is known in the prior art. More specifically, combination toothbrush and toothpaste containers heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 5,842,487; 4,865,481; 5,924,429; ,950,095; 5,769,553; and Des. 407,224.

While these devices fulfill their respective, particular objectives and requirements, the aforementioned patents do not disclose a new dental hygiene assembly. The inventive device includes a main member, a head portion, a refill port and a base portion. The main member has a main chamber for containing a quantity of toothpaste. The head portion has a head chamber that is in fluid communication with the main chamber. The head portion has a plurality of bristles for brushing the teeth of a user. A plurality of bristle apertures are positioned between the plurality of bristles. The bristle apertures are selectively in fluid communication with the head chamber. The refill port is designed to couple to a standard toothpaste container to refill the main chamber. In addition, the base member contains a quantity of dental floss.

In these respects, the dental hygiene assembly according to the present invention substantially departs from the conventional concepts and designs of the prior art, and in so doing provides an apparatus primarily developed for the purpose of combining a toothbrush, a toothpaste container and a dental floss dispenser.

SUMMARY OF THE INVENTION

In view of the foregoing disadvantages inherent in the known types of combination toothbrush and toothpaste containers now present in the prior art, the present invention provides a new dental hygiene assembly construction wherein the same can be utilized for combining a toothbrush, a toothpaste container and a dental floss dispenser.

The general purpose of the present invention, which will be described subsequently in greater detail, is to provide a new dental hygiene assembly apparatus and method which has many of the advantages of the combination toothbrush and toothpaste containers mentioned heretofore and many novel features that result in a new dental hygiene assembly which is not anticipated, rendered obvious, suggested, or even implied by any of the prior art combination toothbrush and toothpaste containers, either alone or in any combination thereof.

To attain this, the present invention generally comprises a main member, a hear portion, a refill port and a base portion. The main member has a main chamber for containing a quantity of toothpaste. The head portion has a head chamber that is in fluid communication with the main chamber. The head portion has a plurality of bristles for brushing the teeth of a user. A plurality of bristle apertures are positioned between the plurality of bristles. The bristle apertures are selectively in fluid communication with the head chamber. The refill port is designed to couple to a standard toothpaste container to refill the main chamber. In addition, the base member contains a quantity of dental floss.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new dental hygiene assembly apparatus and method which has many of the advantages of the combination toothbrush and toothpaste containers mentioned heretofore and many novel features that result in a new dental hygiene assembly which is not anticipated, rendered obvious, suggested, or even implied by any of the prior art combination toothbrush and toothpaste containers, either alone or in any combination thereof.

It is another object of the present invention to provide a new dental hygiene assembly that may be easily and efficiently manufactured and marketed.

It is a further object of the present invention to provide a new dental hygiene assembly that is of a durable and reliable construction.

An even further object of the present invention is to provide a new dental hygiene assembly which is susceptible of a low cost of manufacture with regard to both materials and labor, and which accordingly is then susceptible of low prices of sale to the consuming public, thereby making such dental hygiene assembly economically available to the buying public.

Still yet another object of the present invention is to provide a new dental hygiene assembly which provides in the apparatuses and methods of the prior art some of the advantages thereof, while simultaneously overcoming some of the disadvantages normally associated therewith.

Still another object of the present invention is to provide a new dental hygiene assembly for combining a toothbrush, a toothpaste container and a dental floss dispenser.

Yet another object of the present invention is to provide a new dental hygiene assembly that includes a main member, a head portion, a refill port and a base portion. The main member has a main chamber for containing a quantity of toothpaste. The head portion has a head chamber that is in fluid communication with the main chamber. The head portion has a plurality of bristles for brushing the teeth of a user. A plurality of bristle apertures are positioned between the plurality of bristles. The bristle apertures are selectively in fluid communication with the head chamber. The refill port is designed to couple to a standard toothpaste container to refill the main chamber. In addition, the base member contains a quantity of dental floss.

Still yet another object of the present invention is to provide a new dental hygiene assembly that easy to use.

Even still another object of the present invention is to provide a new dental hygiene assembly that is compact when traveling.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
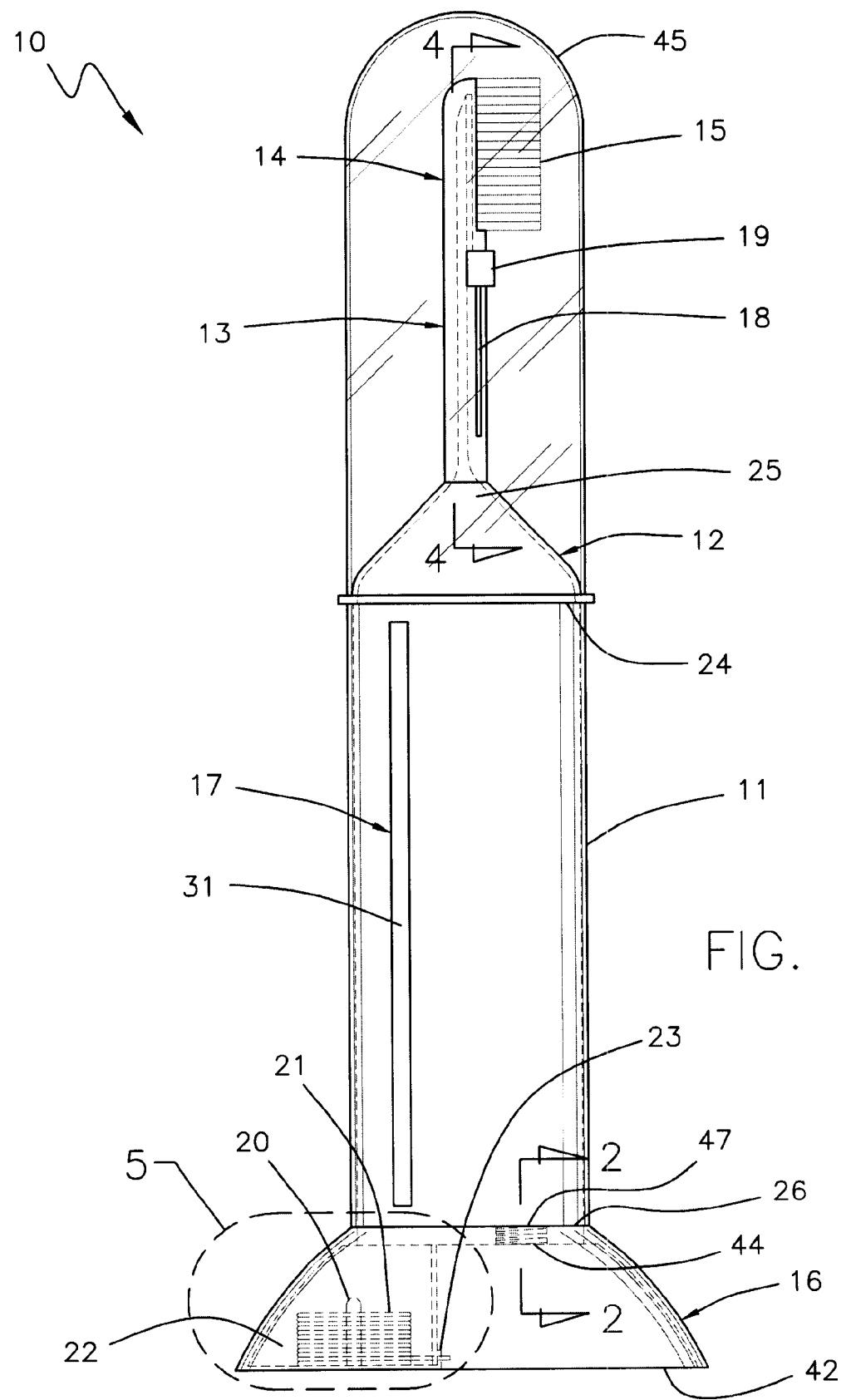
FIG. 1 is a schematic side view of a new dental hygiene assembly according to the present invention.
Figure 2:
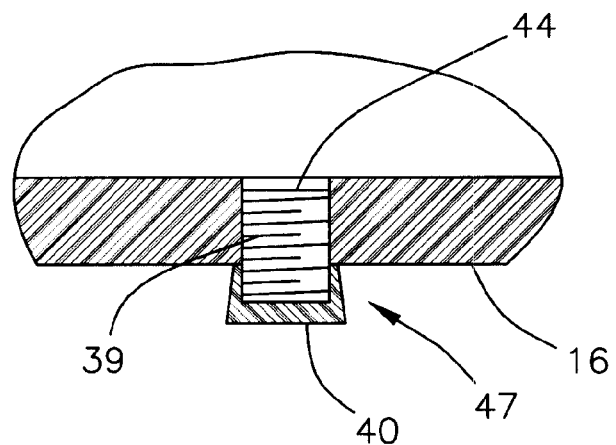
FIG. 2 is a schematic cross-section view of the refill port of the present invention.
Figure 3:
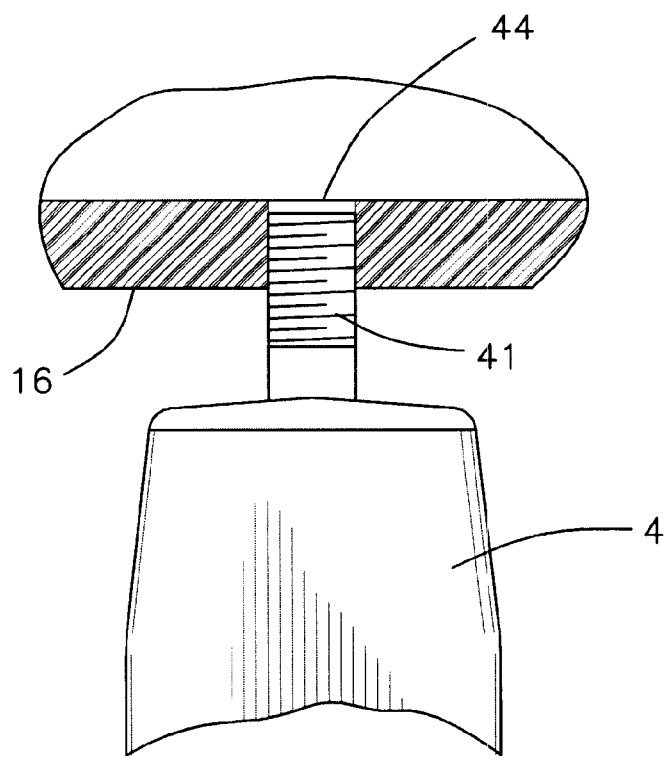
FIG. 3 is a schematic cross-sectional view of the refill port of the present invention engaged to a standard toothpaste container.
Figure 4:
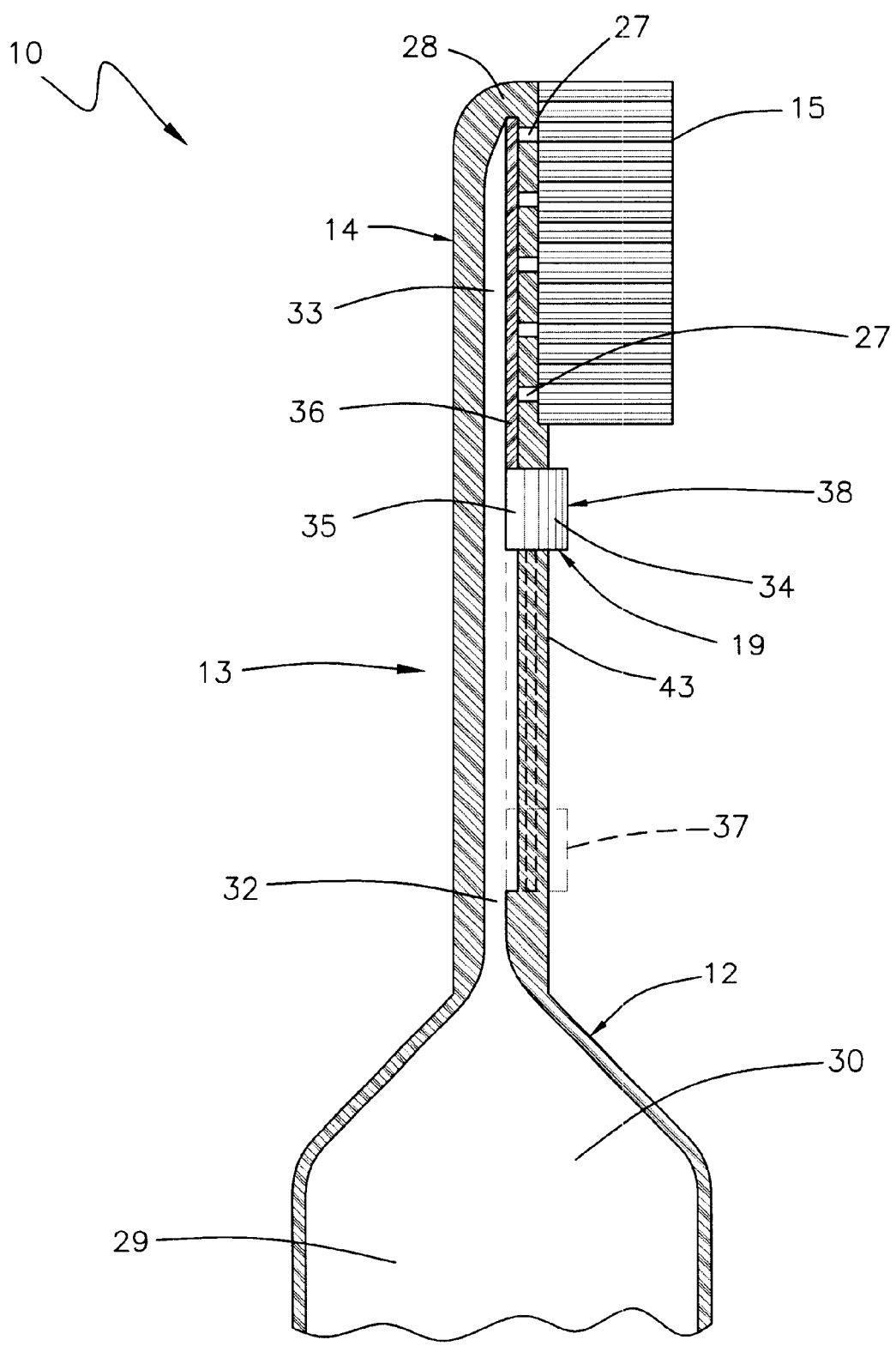
FIG. 4 is a schematic cross-sectional view of the head portion of the present invention.
Figure 5:
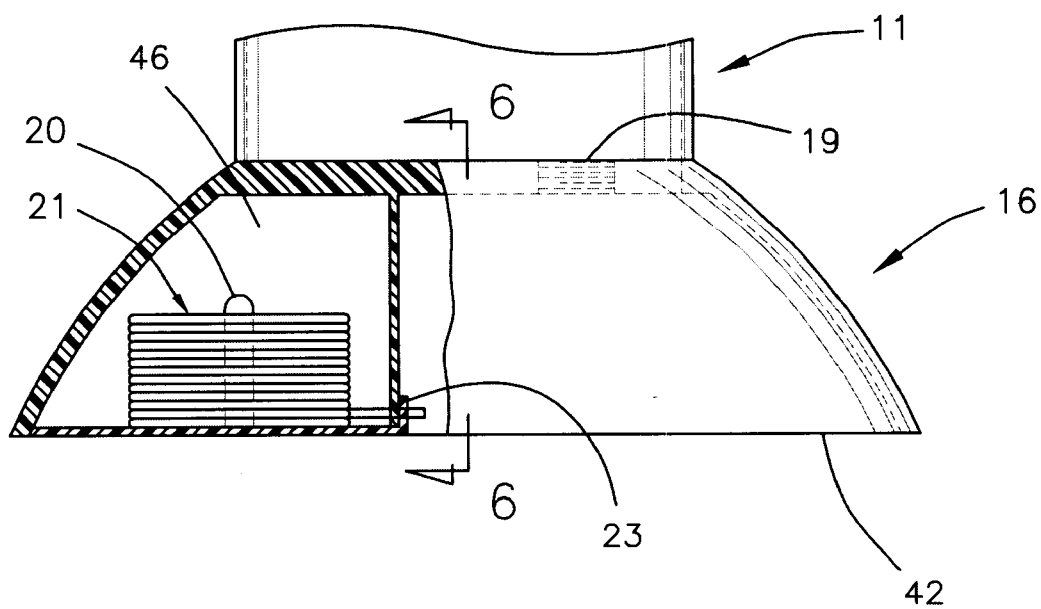
FIG. 5 is a schematic cross-sectional view of the bottom member of the present invention.
Figure 6:
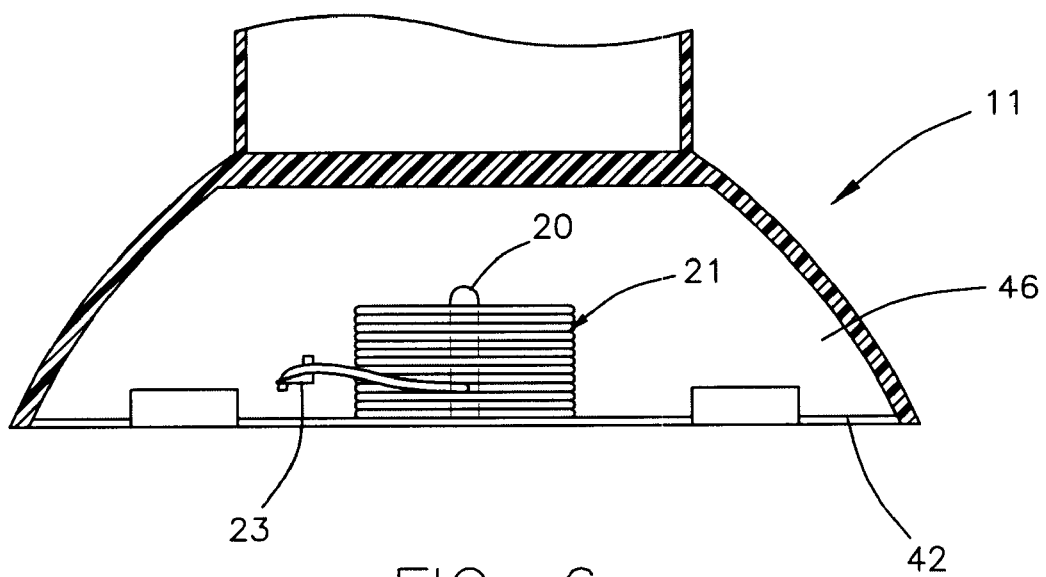
FIG. 6 is a schematic cross-sectional view of the bottom member of the present invention.

With reference now to the drawings, and in particular to FIGS. 1 through 6 thereof, a new dental hygiene assembly embodying the principles and concepts of the present invention and generally designated by the reference numeral 10 will be described.

As best illustrated in FIGS. 1 through 6, the dental hygiene assembly 10 generally comprises a tubular main member 11 that contains a quantity of toothpaste 31, a plurality of bristles 15 for brushing a user's teeth and a base chamber 46 that contains a spool of dental floss 21.

In closer detail, the main member 11 has a main chamber 29 for containing a quantity of toothpaste 31. Extending along the length of the main member 11, is a transparent viewing window 17 for determing the amount of toothpaste 31 contained in the main chamber 29.

A generally tubular frusto-conical crown member 12 extends from a upper end 24 of said main member 11. The crown member 12 has a crown chamber 30 that is in fluid communication with the main chamber 29 of the main member 11.

An elongated neck member 13 extends from a upper end 25 of the crown member 12. The neck member 13 has a neck chamber 32 that is in fluid communication with the crown chamber 29 of the crown portion 12. In addition, a head portion 14 extends from the neck member 13. The head portion 14 has an enclosed distal end 28. The head portion further has a head chamber 33 that is in fluid communication with the neck chamber 32 of the neck member 13.

The plurality of bristles 15 extend from a side of the head portion 14. The head portion 14 also has a plurality of bristle apertures 27 for allowing toothpaste 31 to exit the head portion. The bristle apertures 27 are positioned between the plurality of bristles 15. Moreover, the toothpaste apertures 27 are in fluid communication with the head chamber 33 of the head portion 14.

The main member 11 is made of a semi-pliable material wherein the toothpaste 31 in the main member 11 may be urged through the bristle apertures 27 by squeezing the main member 11.

The neck portion 13 further has an elongated slot 18. The slot 18 extends along a length of the neck member 13 between the crown member 12 and the bristles 15. A lever 19 is engaged in the slot 18. The lever 19 has a first portion 34 that extends out from an external surface 43 of the neck member 13 for allowing manipulation of the lever 19. The lever further has a second portion 35 that is received inside the slot 18. The second portion 35 is coupled to a blocking slat 36. The blocking slat 36 is designed to selectively cover and uncover the bristle apertures 27.

The lever 19 has an open position 37 and a closed position 38. The open position 37 is defined when the lever 19 is positioned away from the bristles 15 thereby allowing the toothpaste 31 to enter the bristle apertures 27. The closed position 38 is defined when the lever 19 is position adjacent the bristles 15 thereby preventing the toothpaste 31 from entering the bristles apertures 27.

A base member 16 extends from a bottom end 26 of the main member 11. The base member 16 has an end surface 42 that is designed to engage a support surface upon which the base member 16 is placed.

The base member further has a refill port 47 for refilling the main chamber 29 of the main member 11 with toothpaste 31. The refill port 47 has a refill aperture 44 that is in fluid communication with the main chamber 29 of the main member. The refill port 47 has internal threads 39 designed to engage the external threads 41 on a standard toothpaste container 4. Thus a standard toothpaste container 4 maybe threadably engaged to the refill port 47 thereby allowing the toothpaste 31 in the standard toothpaste container 4 to be extracted into the main chamber 29 of the main member 11. A refill port cap 40 is used to prevent the toothpaste 31 from escaping from the main chamber 29 of the main member 11 through the refill port 47 when the refill port 47 is not in use. The refill port cap 40 is selectively engaged to the refill port 47.

The base member 16 has a base chamber 46. A spool of dental floss 21 is received inside the base chamber 46 of the base member 16. A holding rod 20 for holding the spool of dental floss 21 is also received inside the base chamber 46 of the base member 16. A cover portion 22 allows access to the base chamber 46 and the spool of dental floss 21. The cover portion 22 is hingably coupled to the base member 16. The base member 16 further has a dental floss aperture 23 for allowing the dental floss 21 to be pulled out of the base chamber 46. The dental floss aperture 23 extends through the base member 16 to the base chamber 46.

A cover member 45 is used for covering the bristles 15 when not in use. The cover member 45 is adapted to selectively engage the upper end 24 of the main member 11. The cover members 45 maybe made of a transparent material or have a decorative design thereon.

In use, the refill port cap 40 is removed from the refill port 47. A standard toothpaste container 4 is then threadably engaged with the internal threads 39 of the refill port 47. The toothpaste 31 in the toothpaste container 4 is then extracted into the main chamber 29 of the main member 11. The refill port cap 40 is then once again engaged to the refill port 47 to stop the toothpaste 31 from flowing out of the main chamber 29 of the main member 11 through the refill port 47.

The cover member 45 is then removed from covering the bristles 15. The lever 19 is then placed in its open position 37. The main member 11 is then squeezed forcing the toothpaste 31 out of the bristle apertures 27. The dental hygiene assembly 10 may then be used to brush a user's teeth. Once finished, the lever 19 is placed in its closed position 38 to stop the flow of toothpaste 31 out of the bristle apertures 27 and to keep the toothpaste 31 from drying out. The cover member 45 is then replaced.

The dental floss 21 maybe accessed by simply pulling on a section of dental floss 21 extending through the dental floss aperture 23 until a desired length is acquired. The dental floss 21 may then be cut off for use.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications arid changes will readily occur to those skilled in the art, it is not desired to limit the invention to the exact construction and operation shown and described, and accordingly, all suitable modifications and equivalents may be resorted to, falling within the scope of the invention.

I claim:

1. A dental hygiene assembly comprising:
   a main member, said main member having a main chamber for containing a quantity of toothpaste;
   a neck member extending from said main member, said neck member having a neck chamber that is in fluid communication with said main chamber of said main member;
   a head portion extending from said neck member, said head portion having an enclosed distal end, said head portion further having a head chamber in fluid communication with said neck chamber of said neck member;
   a plurality of bristles for brushing the teeth of a user said bristles extending from a side of said head portion;
   said head portion having a plurality of bristle apertures for allowing toothpaste to exit said head portion said bristle apertures being positioned between said plurality of bristles, said bristle apertures further being in fluid communication with said head chamber of said head portion;
   said main member being made of a semi-pliable material wherein said toothpaste in said main member may be urged through said bristle apertures by squeezing said main member;
   said neck member further having an elongated slot, said slot extending along a length of said neck member between said main member and said bristles;
   a lever being engaged in said slot, said lever having a first portion that extends out of an external surface of said neck member for allowing manipulation of said lever, said lever further having a second portion received inside said slot;
   a blocking slat being adapted for selectively covering and uncovering said bristle apertures, said blocking slat being coupled to said second portion of said lever;
   said lever having an open position and a closed position, said open position being defined when said lever is positioned away from said bristles thereby allowing said toothpaste to enter said bristle apertures, said closed position being defined when said lever is position adjacent said bristles thereby preventing said toothpaste from entering said bristle apertures;
   said main member including a refill port for refilling said main member with said toothpaste, said refill port having a refill aperture in fluid communication with said main chamber of said main member;
   said refill port having internal threads adapted to engage external threads on a standard toothpaste container wherein said standard toothpaste container may be threadably engaged to said refill port thereby allowing the toothpaste in said standard toothpaste container to be expelled into said main chamber of said main member;
   a refill port cap for preventing said toothpaste from escaping from said main chamber of said main member through said refill port when said refill port is not in use, said refill port cap being selectively engaged to said refill port;
   a base member extending from a bottom end of said main member, said base member having an end surface adapted to engage a support surface upon which said base member is placed, said refill port being positioned in said bottom end of said main member, said refill port cap being positioned between said bottom end of said main member and said end surface of said base member; and
   a generally tubular frusto-conical crown member extending between said main member and said neck member, said crown member having a crown chamber that is in fluid communication with said main chamber of said main member and said neck chamber of said neck member;
   wherein said main member is generally tubular in shape.

2. The dental hygiene assembly of claim 1 further including:

a transparent viewing window for determing the amount of toothpaste contained in the main chamber of the main member, said viewing window extending along a length of said main member.

3. The dental hygiene assembly of claim 1 further comprising:

said base member having a base chamber;

a spool of dental floss being received inside said base chamber of said base member;

a holding rod for holding said spool of dental floss, said holding rod being received inside said base chamber of said base member; and said base member further having a dental floss aperture for allowing said dental floss to be pulled out of said base chamber, said dental floss aperture extending through said base member to said base chamber.

4. The dental hygiene assembly of claim 3 further comprising:

a cover portion for allowing access to said base chamber and said spool of dental floss, said cover portion being hingably coupled to said base member.

5. The dental hygiene assembly of claim 1 wherein said base member is generally frusto-conical in shape.

6. The dental hygiene assembly of claim 1 further comprising:

a cover member for covering said bristles when not in use, said cover member being adapted to selectively engage an upper end of said main member.

7. The dental hygiene assembly of claim 6 wherein said cover member is made of a transparent material.

8. The dental hygiene assembly of claim 6 wherein said cover member has an outer surface that has designs thereon.

9. A dental hygiene assembly comprising:

a tubular main member, said main member having a main chamber for containing a quantity of toothpaste;

a transparent viewing window for determining the amount of toothpaste contained in the main chamber of the main member, said viewing window extending along a length of said main member;

a generally tubular frusto-conical crown member extending from a upper end of said main member, said crown member having a crown chamber that is in fluid communication with said main chamber of said main member;

an elongated neck member extending from a upper end of said crown member, said neck member having a neck chamber that is in fluid communication with said crown chamber of said crown portion;

a head portion extending from said neck member, said head portion having an enclosed distal end, said head portion further having a head chamber in fluid communication with said neck chamber of said neck member;

a plurality of bristles for brushing the teeth of a user, said bristles extending from a side of said head portion;

said head portion having a plurality of bristle apertures for allowing toothpaste to exit said head portion, said bristle apertures being positioned between said plurality of bristles, said toothpaste apertures further being in fluid communication with said head chamber of said head portion;

said main member being made of a semi-pliable material wherein said toothpaste in said main member may be urged through said bristle apertures by squeezing said main member;

said neck portion further having an elongated slot, said slot extending along a length of said neck member between said crown member and said bristles;

a lever being engaged in said slot, said lever having a first portion that extends out from an external surface of said neck member for allowing manipulation of said lever, said lever further having a second portion received inside said slot;

a blocking slat being adapted for selectively covering and uncovering said bristle aperatures, said blocking slat being coupled to said second portion of said lever;

said lever having an open position and a closed position, said open position being defined when said lever is positioned away from said bristles thereby allowing said toothpaste to enter said bristle apertures, said closed position being defined when said lever is position adjacent said bristles thereby preventing said toothpaste from entering said bristles apertures;

a base member further having a refill port for refilling said main chamber of said main member with toothpaste, said refill port being positioned in said bottom end of said main member, said refill port having a refill aperture, said refill aperture being influid communication with said main chamber of said main member;

said refill port having internal threads adapted to engage the external threads on a standard toothpaste container wherein said standard toothpaste container is threadably engaged to said refill port thereby allowing the toothpaste in said standard toothpaste container to be extracted into said main chamber of said main member;

a refill port cap for preventing said toothpaste from escaping from said main chamber of said main member through said refill port when said refill port is not in use, said refill port cap being selectively engaged to said refill port;

said base member having a base chamber;

a spool of dental floss being received inside said base chamber of said base member;

a holding rod for holding said spool of dental floss, said holding rod being received inside said base chamber of said base member;

a cover portion for allowing access to said base chamber and said spool of dental floss, said cover portion being hingably coupled to said base member;

said base member further having a dental floss aperture for allowing said dental floss to be pulled out of said base chamber, said dental floss aperture extending through said base member to said base chamber; and a cover member for covering said bristles when not in use, said cover member being adapted to selectively engage said upper end of said main member, said cover member further being made of a transparent material.

* * * * *